United States Patent [19]

Miyamoto et al.

[11] Patent Number: 4,666,634
[45] Date of Patent: May 19, 1987

[54] VITAMIN D₃ DERIVATIVES HAVING A SUBSTITUENT AT 2-POSITION

[75] Inventors: Katsuhito Miyamoto, Tokyo; Noboru Kubodera; Kiyoshige Ochi, both of Saitama; Isao Matsunaga, Tokyo; Eigoro Murayama, Chiba, all of Japan

[73] Assignee: Chugai Seiyaku Kabushiki Kaisha, Tokyo, Japan

[21] Appl. No.: 800,320

[22] Filed: Nov. 20, 1985

[30] Foreign Application Priority Data

Dec. 5, 1984 [JP] Japan .................................. 59-255713

[51] Int. Cl.⁴ .............................................. C07J 9/00
[52] U.S. Cl. .................................................. 260/397.2
[58] Field of Search ...................................... 260/397.2

[56] References Cited

U.S. PATENT DOCUMENTS 4,011,250 3/1977 Ishikawa et al. ................. 260/397.2

FOREIGN PATENT DOCUMENTS 2535308 2/1976 Fed. Rep. of Germany ... 260/397.2
50-100043 8/1975 Japan .
50-100044 8/1975 Japan .

Primary Examiner—Leonard Schenkman
Assistant Examiner—Joseph A. Lipovsky
Attorney, Agent, or Firm—Browdy and Neimark

[57] ABSTRACT

A 1α-hydroxy vitamin D₃ derivative of the formula:

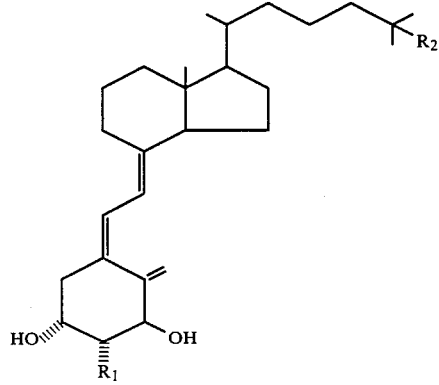

where $R_1$ is a hydroxyl group, an amino group or the group: OR' (where R' is a lower alkyl group having 1 to 7 carbon atoms that may or may not be substituted by a hydroxyl group, a halogen atom, a cyano group, a lower alkoxy group having 1 to 3 carbon atoms, an amino group, or an acylamino group); $R_2$ is a hydrogen atom or a hydroxyl group), and a process for preparing the same are disclosed.

The compound represented by the formula above has the calcium control action and the ability to induce differentiation in tumor cells and, therefore, are useful as an antitumor agents and a medicine for treating calcium dysbolism-caused diseases.

10 Claims, No Drawings

VITAMIN D₃ DERIVATIVES HAVING A SUBSTITUENT AT 2-POSITION

The present invention relates to novel vitamin D₃ derivatives that have calcium control action and the ability to induce differentiation in tumor cells and which are useful both as antitumor agents and as medicines for the treating calcium dysbolism-caused diseases such as osteoporosis and osteomalacia. More specifically, the present invention relates to such vitamin D₃ derivatives having a substituent at 2β-position.

While many vitamin D₃ compounds are known in the art, they are generally classified as naturally occurring vitamin D₃ metabolities (e.g. 25-hydroxy vitamin D₃, 1α,25-dihydroxy vitamin D₃ and 1α,24,25-trihydroxy vitamin D₃) and their synthetic analogs (e.g. 1α-hydroxy vitamin D₃, 1α,24-dihydroxy vitamin D₃, and a variety of fluorinated vitamin D₃ compounds). Among these known vitamin D₃ compounds, the naturally occurring 1α,25-dihydroxy vitamin D₃ and a synthetic analog wherein the side chain attached to 17-position of vitamin D₃ is fluorinated such as 24,24-difluoro-1α,25-dihydroxy vitamin D₃ have a strong calcium control action and are useful in treatment of various bone disorders.

While studying a variety of vitamin D₃ derivatives, the present inventors have found that certain vitamin D₃ derivatives having a substitutent at 2-position, especially at 2β-position, exhibit a strength comparable to 1α,25-dihydroxy vitamin D₃ in terms of the in vivo calcium control action.

The 1α-hydroxy vitamin D₃ derivative having a substituent at 2β-position is represented by the following formula (I):

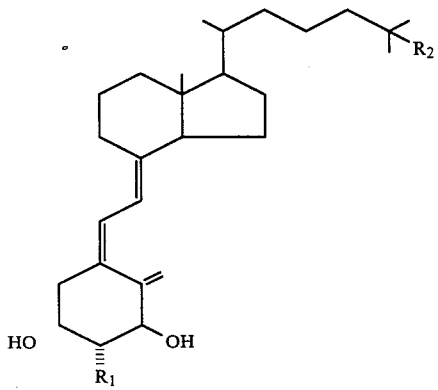

where R₁ is a hydroxyl group, an amino group or the group OR' (where R' is a lower alkyl group which may or may not be substituted by a hydroxyl group, a halogen atom, a cyano group, a lower alkoxy group, an amino group or an acylamino group); and R² is a hydrogen atom or a hydroxyl group.

Examples of the lower alkyl group represented by R' in formula (I) are branched- or straight-chain alkyl groups having 1 to 7 carbon atoms, and these alkyl groups may be substituted at a desired position by a hydroxyl group, a halogen such as bromine or chlorine, a cyano group, a lower alkoxy group having 1-3 carbon atoms, an amino group, or an acylamino group.

The 1α-hydroxy vitamin D₃ compounds of the formula (I) are novel and may be synthesized by the following procedures:

(1) a cyclized adduct of 1,5,7-cholestatrien-3β-ol and 4-phenyl-1,2,4-triazoline-3,5-dione is prepared from cholesterol or 25-hydroxy-cholesterol according to the description in Unexamined Published Japanese Patent Application Nos. 84555/1975 and 84560/1975;

(2) the cyclized adduct is converted to a 1α,2α-epoxide (compound 1) having the formula shown below:

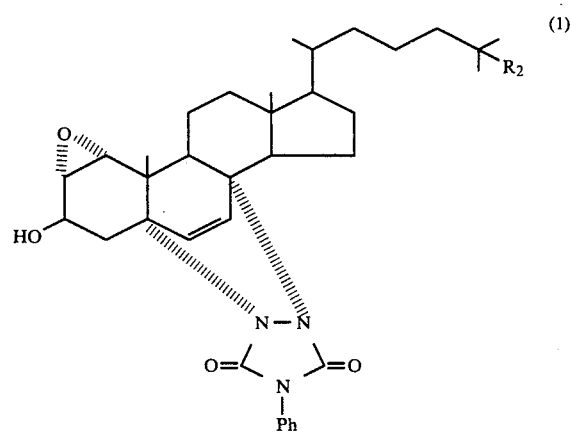

(where R₂ is a hydrogen atom or a hydroxyl group; and Ph is a phenyl group);

(3) the epoxide (compound 1) is reacted with a nucleophilic reagent, such as an alcohol, of the formula: R'OH (where R' is the same as defined above) in an inert solvent in the presence of an acid catalyst such as p-toluenesulfonic acid to obtain a compound of formula (II):

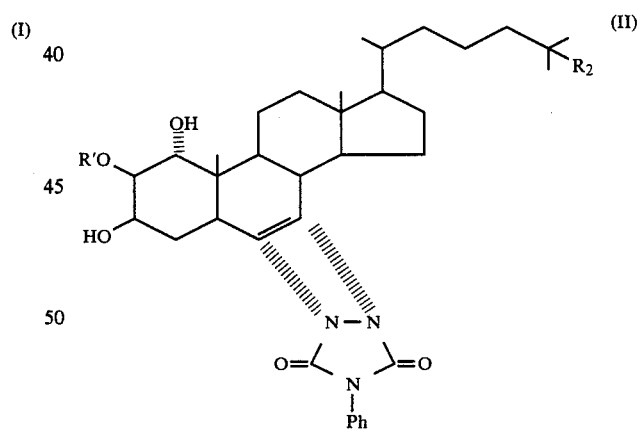

(where R', R₂ and Ph are respectivly the same as defined above); and (4) the compound (II) is subjected to the process shown in Unexamined Published Japanese Patent Application No. 84555/1975 that consists of elimination of the triazoline-3,5-dione ring, exposure to radiation and isomerization, whereby the compound of formula (I) is obtained.

By reacting the epoxide (compound 1) with water rather than an alcohol as a nucleophilic reagent, a compound (II) having a hydroxyl group at 2-position is obtained. If sodium azide is used as the nucleophilic reagent, a compound (II) having an azido group at 2-position is obtained. These compounds are subjected to step (4) to obtain compounds of formula (I) wherein $R_1$ is a hydroxyl group and an amino group, respectively. The azido group at 2-position of compound (II) may be converted to an amino group by subjecting said compound to reduction with lithium aluminum hydride simultaneously with the elimination of the 1,2,4-triazoline ring.

PHARMACOLOGICAL ACTIONS OF COMPOUND (I)

The compounds of the present invention were found to have the calcium control action and the ability to induce differentiation in tumor cells by the following experiments.

(A) Calcium control action (i) Male weanling Spraque Dawley rats weighing 45–50 g were fed Diet 11 and deionized water under an incandescent lamp for 3 weeks. The compound of the present invention (as prepared in Example 4), and a control 1α,25-dihydroxy vitamin $D_3$ (1α,25-$(OH)_2D_3$), which were respectively dissolved in ethanol, were administered intravenously into the aminals. The animals were then starved for 24 hours and blood samples were drawn from the heart of each rat. Plasma was isolated from each blood sample and the contents of calcium and inorganic phosphorus were measured by the OCPC method described in Am. J. Clin. Path., 45, 290 (1966) and Biochem. J., 65, 709 (1957). The results are shown in Table 1.

TABLE 1

| Compound | Dose | Calcium in plasma (mg/dl) | Inorganic P in plasma (mg/dl) |
|---|---|---|---|
| EtOH only | 0.5 mg/kg | 4.796 ± 0.207 | 9.403 ± 1.517 |
| Compound of Example 4 | 6.25 μg/ 0.5 ml/kg | 5.916 ± 0.323*** | 8.533 ± 0.687 |
|  | 12.5 μg/ 0.5 ml/kg | 6.058 ± 0.551*** | 8.503 ± 1.387 |
| 1α,25-$(OH)_2$-$D_3$ | 1.25 μg/ 0.5 ml/kg | 5.463 ± 0.290** | 7.561 ± 0.477* |
|  | 2.5 μg/ 0.5 ml/kg | 5.506 ± 0.324** | 9.066 ± 1.906 |

***$p < 0.001$
**$p < 0.01$
*$p < 0.05$ (ii) The same rats as described in (i) were fed in the same manner as shown in (i).

Two compounds of the present invention (as prepared in Examples 4 and 6) and two controls, 1α-hydroxy vitamin $D_3$ (1α-OH-$D_3$) and 25-hydroxy vitamin $D_3$ (25-OH-$D_3$), were administered orally to the rats for 5 consecutive days after being dissolved in triglyceride of medium-chain aliphatic acid (MCT). The rats given the last dose were starved for 24 hours and blood samples were drawn from the heart of each rat. The contents of calcium and inorganic phosphorus in plasma were measured by the same method as used in (i). The results are shown in Table 2.

TABLE 2

| Compound | Dose | Calcium in plasma (mg/dl) | Inorganic P in plasma (mg/dl) |
|---|---|---|---|
| MCT only | 1 mg/kg | 4.263 ± 0.235 | 7.488 ± 0.933 |
| Compound of Example 4 | 6.25 μg/ml/kg | 5.552 ± 0.912* | 8.713 ± 1.648 |
| Compound of Example 6 | 6.25 μg/ml/kg | 8.093 ± 0.648*** | 7.040 ± 0.595 |
| 1α-OH-$D_3$ | 6.25 μg/ml/kg | 4.798 ± 0.582 | 7.776 ± 0.682 |
| 25-OH-$D_3$ | 6.25 μg/ml/kg | 5.682 ± 0.364*** | 9.115 ± 0.647** |

***$p < 0.001$
**$p < 0.01$
*$p < 0.05$

(B) Induction of differentiation (i) Morphological change

Human promyelocytic leukemia cells (HL-60 cell line) were cultured in an RPMI-1640 medium supplemented with 10% heat-inactivated fetal calf serum under 5% $CO_2$/95% air at 37° C. To the so prepared medium, ethanol solutions of the compound obtained in Example 4 and control 1α-hydroxy vitamin $D_3$ were added in such a manner that the ethanol concentration in the liquid medium was 0.1%. Upon addition of the compound in Example 4 and the control, the HL-60 cells were found to differentiate into macrophage-like cells by morphological observation on 3 days. The percentage of the HL-60 cells that underwent differentiation was determined by counting their number.

At least 60% of the HL-60 cells treated with the compound of Example 4 in doses of the order of $10^{-6}$–$10^{-7}$M were differentiated into macrophages, suggesting that said compound had a differentiation-inducing ability comparable to that of the control 1α-hydroxy vitamin $D_3$.

(ii) NBT-reduced cell induction ability

To HL-60 cells, the compound prepared as in Example 4 was added for a period of 4–5 days. To the treated cells, TPA (12-O-tetradecanoylphorbol-13-acetate) and NBT (nitro blue tetrazolium) were added in respective final concentrations of 100 ng/ml and 0.1%. After standing for 20 minutes at 37° C., the percentage of the HL-60 cells that were differentiated into macrophages and reduced NBT to form formazan was determined. Both the compound of Example 4 and the control 1α-hydroxy vitamin $D_3$ exhibited a differentiation-inducing ability of 95% upward in a dose of $10^{-6}$M.

The following examples are provided for the purpose of further illustrating the present invention and are by no means intended as limiting.

EXAMPLE 1

Production of 1α-hydroxy-2β-methoxy vitamin $D_3$ (a) Preparation of a Diels-Alder adduct of 2β-methoxy-5,7-cholestadiene-1α,3β-diol and 4-phenyl-1,2,4-triazoline-3,5-dione Five hundred milligrams (0.871 mmol) of the 1α,2α-epoxide compound 1 ($R_2$=H) was dissolved in 4 ml of dry tetrahydrofuran. To the solution, 10 ml of methanol and 35 mg (0.184 mmol) of p-toluene sulfonic acid were added and the mixture was heated under reflux for 5 hours. To the cooled mixture, ethyl acetate was added and the organic layer was washed successively with water, an aqueous solution of sodium hydrogencarbonate and water. After drying over magnesium sulfate, the solvent was distilled off. The residue was subjected to silica gel column chromatography and eluted with chloroform containing 20% (v/v) acetone, producing 240.2 mg of the end compound.

NMR spectrum δ(CDCl$_3$): 0.80 (3H, s), 0.90 (3H, s), 3.43 (3H, s), 4.65 (1H, m), 6.07 and 6.33 (2H, AB, J=15.6, 7.08 Hz), 7.28 (5H, m).

(b) Preparation of 2β-methoxy-5,7-cholestadiene-1α,3β-diol

A portion (229 mg, or 0.378 mmol) of the Diels-Alder adduct of 2β-methoxy-5,7-cholestadiene-1α,3β-diol and 4-phenyl-1,2,4-triazoline-3,5-dione prepared in (a) was dissolved in 10 ml of dry tetrahydrofuran in an argon atmosphere and the solution was stirred at room temperature. After gradual addition of 60 mg (1.58 mmol) of lithium aluminum hydride, the mixture was refluxed for 1 hour. To the ice-cooled reaction mixture, a saturated aqueous solution of sodium sulfate was added dropwise under agitation to quench excess lithium aluminum hydride. The gel was removed by filtration under suction and the tetrahydrofuran was distilled off. The residue was subjected to extraction with ethyl acetate, washed successively with dilute hydrochloric acid and water, and dried over magnesium sulfate. The solvent was distilled off and the residue was subjected to silica gel column chromatography. Upon elution with chloroform, 86 mg of the end compound was obtained.

UV spectrum $\lambda_{max}^{EtOH}$ (nm): 292, 281, 270, 262 (sh).

(c) Preparation of 1α-hydroxy-2β-methoxy vinamin D$_3$

Eighty-six milligrams (0.20 mmol) of the 2β-methoxy-5,7-cholestadiene-1α,3β-diol obtained in (b) was dissolved in 400 ml of ethanol of guaranteed quality. Under ice-cooling in an argon atmosphere, the solution was irradiated for 3 minutes by a 200 W mercury lamp through a Vycor glass filter. After removal of the solvent under vacuum, the residue was dissolved in 10 ml of anhydrous tetrahydrofuran, and the mixture was heated under reflux for 1 hour. After cooling, the solvent was distilled off and the residue was subjected to column chromatography using Sephadex LH-20 (Pharmacia Fine Chemicals). Upon elution was a 65:35 mixture of chloroform and hexane, 14.0 mg of the end compound of the present invention was obtained as an oil.

UV spectrum $\lambda_{max}^{EtOH}$ (nm): 263.5.
Mass spectrum (m/e): 430 (M+), 412, 398, 380, 150.

EXAMPLE 2

1α-hydroxy-2β-ethoxy vitamin D$_3$ (a) Preparation of Diels-Alder adduct of 2β-ethoxy-5,7-cholestadiene-1α,3β-diol and 4-phenyl-1,2,4-triazoline-3,5-dione A portion (506 mg, or 0.882 mmol) of the compound 1 (R$_2$=H) used in Example 1(a) was dissolved in dry tetrahydrofuran (6 ml). To the solution, 12 ml of ethanol and 68 mg (0.357 mmol) of p-toluenesulfonic acid were added and the mixture was stirred for 2 days at room temperature. The stirred mixture was subsequently treated as in Example 1(a) to give 172 mg of the end compound.

NMR spectrum δ(CDCl$_3$): 0.90 (3H, s) 6.12 and 6.32 (2H, AB, J=8.0 Hz) 7.32 (5H, m).

(b) Preparation of 2β-ethoxy-5,7-cholestadiene-1α3β-diol

The compound (172 mg, or 0.277 mmol) obtained in (a) was dissolved in 15 ml of dry tetrahydrofuran in an argon atmosphere, and the solution was stirred at room temperature. After gradual addition of 154 mg (4.06 mmol) of lithium aluminum hydride, the mixture was refluxed for 1 hour. To the ice-cooled reaction mixture, a solution of sodium hydroxide was added dropwise under agitation to quench excess lithium aluminum hydride. The mixture was subsequently treated as in Example 1(b) to give 60.1 mg of the end compound.

UV spectrum $\lambda_{max}^{EtOH}$ (nm): 293, 281, 271, 262 (sh).
NMR spectrum (CDCl$_3$): 0.62 (3H, s), 0.81 (3H, s), 1.05 (3H, t), 3.68 (2H, q), 5.31 and 5.67 (2H, AB, J=6.0 Hz).

(c) Preparation of 2β-ethoxy-1α-hydroxy vitamin D$_3$

The 2β-ethoxy-5,7-cholestadiene-1α,3β-diol (60.1 mg, or 0.135 mmol) obtained in (b) was treated as in Example 1(c) to obtain 10.5 mg of the end compound.

UV spectrum $\lambda_{max}^{EtOH}$ (nm): 264.
Mass spectrum (m/e): 444 (M+), 426, 398, 380, 150.

EXAMPLE 3

1α-hydroxy-2β-isobutoxy vitamin D$_3$

The end compound was obtained by repeating the procedures of Examples 1(a) thru (c) except that the methanol used in Example 1(a) was replaced by isobutyl alcohol.

UV spectrum $\lambda_{max}^{EtOH}$ (nm): 265.
Mass spectrum (m/e): 416 (M+), 398, 380, 150.

EXAMPLE 4

1α-hydroxy-2β-(2-hydroxyethoxy) vitamin D$_3$ (a) Preparation of Diels-Alder adduct of 2β-(2-hydroxyethoxy)-5,7-cholestadiene-1α,3β-diol and 4-phenyl-1,2,4-triazoline-3,5-dione (i) Using ethylene glycol:
A portion (265 mg, or 0.462 mmol) of the compound 1 (R$_2$=H) used in Example 1(a), 5 ml of dry tetrahydrofuran, 10 ml of ethylene glycol, and 37 mg (0.195 mmol) of p-toluenesulfonic acid were treated as in Example 1(a) to obtain the end compound.

NMR spectrum δ(CDCl$_3$): 0.80 (3H, s), 0.90 (3H, s), 3.56 (2H, m), 3.74 (2H, m), 4.57 (1H, m), 6.9 and 6.29 (2H, AB, J=9.0 Hz), 7.29 (5H, m).

(ii) Using a dioxolane compound:
A portion (102 mg, or 0.178 mmol) of the compound 1 used in Example 1(a) was dissolved in 2 ml of dry tetrahydrofuran. To the solution, 1.0 ml (9.30 mmol) of 2,2-dimethyl-1,3-dioxolane and 100 μl of boron trifluoride etherate were added and the mixture was stirred for 20 hours at room temperature. After addition of ethyl acetate, the mixture was washed with water and dried over magnesium sulfate, followed by the distilling off of the solvent. The residue was subjected to silica gel column chromatography and eluted with chloroform containing 20% (v/v) acetone, producing 21.3 mg of the end compound which had the same physical data as those of the compound obtained in (i).

(b) Preparation of 2β-(2-hydroxyethoxy)-5,7-cholestadiene-1α,3β-diol

A portion (398.5 mg, or 0.627 mmol) of the Diels-Alder adduct obtained in (i) or (ii) of (a) above was treated as in Example 1(b) using 40 ml of dry tetrahydrofuran and 333 mg (8.77 mmol) of lithium aluminum hydride. The end compound was obtained in an amount of 173.2 mg.

UV spectrum $\lambda_{max}^{EtOH}$ (nm): 293.5, 281.5, 271, 262 (sh).

NMR spectrum (CDCl$_3$): 0.55 (3H, s), 0.83 (3H, s), 0.91 (6H, s), 5.30 and 5.62 (2H, AB, J=6.0 Hz).

(c) Preparation of 1α-hydroxy-2-(2-hydroxyethoxy) vitamin D$_3$

A portion (173 mg, or 0.376 mmol) of the 2β-(2-hydroxyethoxy)-5,7-cholestadiene-1α,3β-diol obtained in (b) was treated as in Example 1(c) to produce 39.9 mg of the end compound.

UV spectrum $\lambda_{max}^{EtOH}$ (nm): 262.5.

Mass spectrum (m/e): 460 (M+), 442, 398, 380, 150.

FT-NMR spectrum (CDCl$_3$): 0.55 (3H, s), 0.86 (6H, d, J=6.6 Hz), 0.92 (3H, d, J=6.4 Hz), 3.33 (1H, dd), 3.65-3.90 (1H, m), 4.23 (1H, m), 4.37 (1H, d, J=8.4 Hz), 5.09 (1H, s), 5.49 (1H, s), 6.04 (1H, d, J=12.6 Hz), 6.37 (1H, d, J=12.6 Hz)

EXAMPLES 5 TO 10

The compound listed below were obtained by repeaning the procedures of Example 1(a) thru (c) except that the methanol used in Example 1(a) was replaced by ethylene bromohydrin (Example 5), trimethylene glycol (Example 6), 4-methyl-1,4-pentanediol (Example 7), ethylene cyanohydrin (Example 8), water (Example 9) and 1,4-butanediol (Example 10).

EXAMPLE 5

2β-(2-bromoethoxy-1α-hydroxy vitamin D$_3$

UV spectrum $\lambda_{max}^{EtOH}$ (nm): 264.

Mass spectrum (m/e): 446 (M+ −Br), 428, 400, 382, 134.

EXAMPLE 6

1α-hydroxy-2β-(3-hydroxypropoxy) vitamin D$_3$

UV spectrum $\lambda_{max}^{EtOH}$ (nm): 263.

Mass spectrum (m/e): 474 (M+), 456, 398, 380, 150.

EXAMPLE 7

1α-hydroxy-2β-(4-hydroxy-4-methylpentoxy) vitamin D$_3$

UV spectrum $\lambda_{max}^{EtOH}$ (nm): 263.

Mass spectrum (m/e): 517 (M+ +1), 500, 398, 380, 150, 83, 59.

EXAMPLE 8

2β-(2-cyanoethoxy)-1α-hydroxy vitamin D$_3$

UV spectrum $\lambda_{max}^{EtOH}$ (nm): 262.

Mass spectrum (m/e): 469 (M+), 416, 398, 380, 150.

EXAMPLE 9

1α,2β-dihydroxy Vitamin D$_3$

UV spectrum $\lambda_{max}^{EtOH}$ (nm): 263.

Mass spectrum (m/e): 416 (M+), 398, 380, 150.

EXAMPLE 10

1α-hydroxy-2β-(4-hydroxybutoxy) vitamin D$_3$

UV spectrum $\lambda_{max}^{EtOH}$ (nm): 263.5.

Mass spectrum (m/e): 488 (M+), 470, 452, 150.

EXAMPLE 11

2β-(2-N-acetylaminoethoxy)-1α-hydroxy vitamin D$_3$ (a) Preparation of 1α,2α-epoxy-5,7-cholestadin-3β-ol A portion (2.05 g, or 3.57 mmol) of the compound 1 (R$_2$=H) used in Example 1(a) was dissolved in 100 ml of dry dimethylformamide. After addition of 0.92 g (3.51 mmol) of triphenylphosphine, the solution was heated on a bath (90°-100° C.) for 10 hours under agitation. The reaction mixture was poured into ice water and subjected to extraction with ethyl acetate. The organic layer was washed with water and dried over magnesium sulfate, followed by the distilling off of the solvent. The residue was subjected to silica gel column chromatography and eluted with chloroform containing 20% (v/v) acetone, thereby providing 1.29 g of the end compound.

UV spectrum $\lambda_{max}^{EtOH}$ (nm): 290, 279, 269, 261 (sh).

NMR spectrum (CDCl$_3$): 0.63 (3H, s), 0.82 (3H, s), 0.91 (6H, s), 5.36 and 5.66 (2H, AB, J=6.0 Hz).

(b) Preparation of 2β-(2-N-acetylaminoethoxy)-5,7-cholestadiene-1α,3β-diol

A portion (397 mg, or 0.996 mmol) of the 1α,2α-epoxy-5,7-cholestadin-3β-ol obtained in (a) was dissolved in 8 ml of dry tetrahydrofuran in an argon atmosphere. After addition of 2-N-acetylaminoethanol (3 ml), the mixture was stirred at room temperature. To the mixture, 0.2 ml of boron trifluoride etherate was added dropwise and the resultant mixture was stirred for 10 hours at room temperature, followed by refluxing for 7 hours. After cooling, ethyl acetate was added to the reaction mixture. The organic layer was washed with water and dried over magnesium sulfate, followed by the distilling off of the solvent. The residue was subjected to silica gel column chromatography and eluted with chloroform containing 20% (v/v) acetone, producing 32.6 mg of the end compound.

NMR spectrum δ(CDCl$_3$:CD$_3$OD=3:1): 0.64 (3H, s), 0.81 (3H, s), 0.90 (6H, s), 2.07 (3H, s), 3.34 (2H, m), 3.68 (2H, m), 5.28 and 5.60 (2H, AB, J=6.0 Hz).

(c) Preparation of 2β-(2-N-acetylaminoethoxy)1α-hydroxy vitamin D$_3$

The 2β-(2-N-acetylaminoethoxy)-5,7-cholestadiene-1α,3β-diol (32.6 mg, or 6.50×10$^{-2}$ mmol) obtained in (b) was treated as in Example 1(c) to obtain 6.96 mg of the end compound.

UV spectrum $\lambda_{max}^{EtOH}$ (nm): 262.5.

Mass spectrum (m/e): 458 (M+ −CH$_3$CO), 440, 398, 383, 150, 43.

EXAMPLE 12

2β-amino-1α-hydroxy vitamin D$_3$ (a) Preparation of Diels-Alder adduct of 2β-azido-5,7-cholestadiene-1α,3β-diol and 4-phenyl-1,2,4-triazoline-3,5-dione A portion (501 mg, or 0.873 mmol) of the compound 1 (R$_2$=H) used in Example 1(a) was dissolved in 10 ml of dioxane in an argon atmosphere and the solution was refluxed. To the solution, 102 mg (1.57 mmol) of sodium azide as dissolved in 2.6 ml of water was added dropwise, and the resultant mixture was refluxed for 10 hours. After cooling, the mixture was subjected to extraction with ethyl acetate, washed with water and dried over magnesium sulfate. After distilling off the solvent, the residue was subjected to silica gel column chromatography and eluted with chloroform containing 20% (v/v) acetone, to give 81.9 mg of the end compound.

IR spectrum $\nu$max (cm$^{-1}$): 2250.

NMR spectrum $\delta$(CDCl$_3$): 0.81 (3H, s), 0.90 (3H, s), 6.15 and 6.33 (2H, AB, J=8.0 Hz), 7.33 (5H, m).

(b) Preparation of 2$\beta$-amino-5,7-cholestadiene-1$\alpha$,3$\beta$-diol

The Diels-Alder adduct (81.9 mg, or 0.133 mmol) obtained in (a), 10 ml of dry tetrahydrofuran and 94 mg (2.48 mmol) of lithium aluminum hydride were treated as in Example 1(b) to produce 39.5 mg of the end compound.

UV spectrum $\lambda_{max}^{EtOH}$ (nm): 292.5, 281, 271, 262 (sh).

IR spectrum $\nu$max (cm$^{-1}$): 3500, 3320, 3210.

NMR spectrum $\delta$(CDCl$_3$:CD$_3$OD=3:1): 0.62 (3H, s) 0.83 (3H, s), 0.92 (6H, s), 5.37 and 5.59 (2H, AB, J=13.2, 6.0 Hz).

(c) Preparation of 2$\beta$-amino-1$\alpha$-hydroxy vitamin D$_3$

The 2$\beta$-amino-5,7-cholestadiene-3$\beta$-ol (39.5 mg, or 0.0095 mmol) obtained in (b) was treated as in Example 1(c) to produce 6.28 mg of the end compound.

UV spectrum $\lambda_{max}^{EtOH}$ (nm): 266.

Mass spectrum (m/e): 416 (M$^+$+1), 400, 382, 367, 134.

EXAMPLES 13 AND 14

Compound 1 (R$_2$=OH) which had been prepared from 25-hydroxycholesterol was treated as in Example 1(a), (b) and (c) to produce the following compounds.

EXAMPLE 13

1$\alpha$,25-dihydroxy-2$\beta$-(3-hydroxypropoxy) vitamin D$_3$

UV spectrum $\lambda_{max}^{EtOH}$ (nm): 263.
Mass spectrum (m/e): 490 (M$^+$), 472, 454, 59.

EXAMPLE 14

1$\alpha$,25-dihydroxy-2$\beta$-(2-hydroxyethoxy) Vitamin D$_3$

UV spectrum $\lambda_{mas}^{EtOH}$ (nm): 262.
Mass spectrum (m/e): 476 (M$^+$), 458, 440, 59.

What is claimed is:

1. A 1$\alpha$-hydroxy vitamin D$_3$ derivative of the formula:

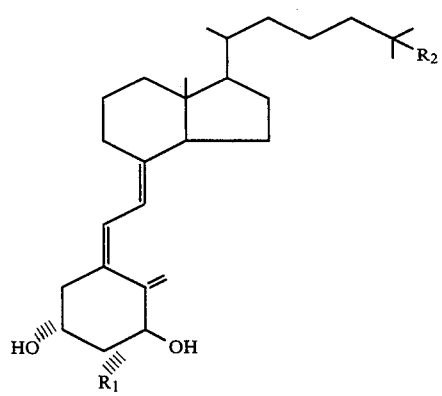

where R$_1$ is an amino group or the group: OR' where R' is an unsubstituted lower alkyl group having 1 to 7 carbon atoms or loweralkyl substituted by a hydroxyl group, a halogen atom, a cyano group, a lower alkoxy group having 1 to 3 carbon atoms, an amino group, or an acylamino group; R$_2$ is a hydrogen atom or a hydroxyl group.

2. A compound according to claim 1 which is represented by the formula:

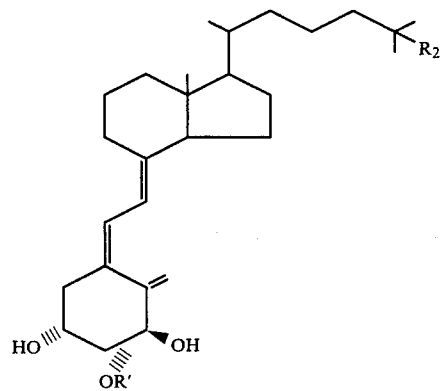

where R$_2$ and R' have the same meanings as defined in claim 1.

3. A compound according to claim 2 wherein R$_2$ is a hydrogen atom.

4. A compound according to claim 2 wherein R$_2$ is a hydroxyl group.

5. A compound according to claim 1 wherein R$_2$ is a hydroxyl group.

6. A compound according to claim 1 wherein R$_2$ is a hydrogen atom.

7. A compound which is represented by the formula:

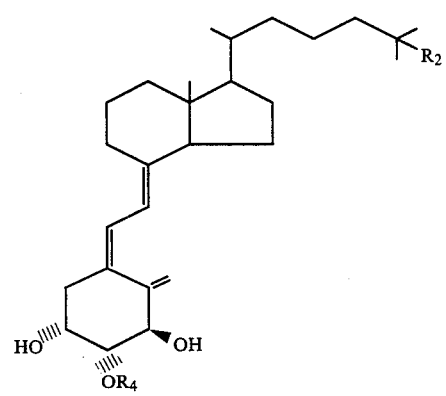

where R$_2$ is a hydrogen atom or hydroxyl group; R$_4$ is a hydroxyl-substituted lower alkyl group having 1 to 7 carbon atoms.

8. A compound according to claim 7 wherein R$_2$ is a hydrogen atom.

9. A compound according to claim 7 wherein R$_2$ is a hydroxyl group.

10. A 1$\alpha$-hydroxy vitamin D$_3$ derivative of the formula:

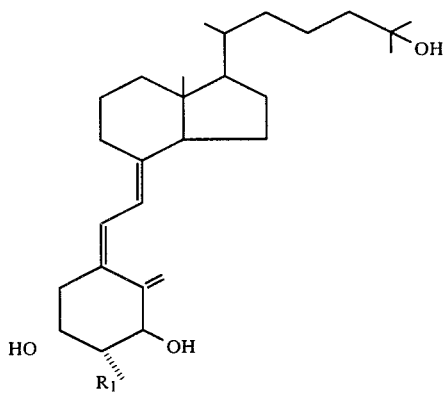
where $R_1$ is a hydroxyl group, an amino group or the group: OR' where R' is a lower alkyl group having 1 to 7 carbon atoms that may or may not be substituted by a hydroxyl group, a halogen atom, a cyano group, a lower alkoxy group having 1 to 3 carbon atoms, an amino group, or an acylamino group.
* * * * *